(12) United States Patent
Larnard et al.

(10) Patent No.: US 6,743,200 B2
(45) Date of Patent: Jun. 1, 2004

(54) EXPANDABLE DEVICE FOR THERMAL THERAPY

(75) Inventors: Donald J. Larnard, Hampton Falls, NH (US); Dan Sachs, Boston, MA (US)

(73) Assignee: Seacoast Technologies, Inc., Portsmouth, NH (US)

( * ) Notice: Subject to any disclaimer, the term of this patent is extended or adjusted under 35 U.S.C. 154(b) by 83 days.

(21) Appl. No.: 09/971,015

(22) Filed: Oct. 4, 2001

(65) Prior Publication Data

US 2002/0091428 A1 Jul. 11, 2002

Related U.S. Application Data (60) Provisional application No. 60/238,314, filed on Oct. 5, 2000.

(51) Int. Cl.[7] .............................. A61F 7/12; A61M 31/00
(52) U.S. Cl. .............. 604/113; 604/103.07; 604/103.08
(58) Field of Search ........................ 604/103.07, 113, 604/103.11, 912, 916, 503, 103.08; 600/31

(56) References Cited

U.S. PATENT DOCUMENTS

| | | | |
|---|---|---|---|
| 2,190,384 A | * 2/1940 | Newman | 607/105 |
| 3,170,465 A | 2/1965 | Henney et al. | 128/401 |
| 3,174,481 A | * 3/1965 | Seaman | 607/105 |
| 3,220,414 A | 11/1965 | Johnston | 128/400 |
| 3,504,674 A | 4/1970 | Swenson et al. | 128/303.1 |
| 3,736,936 A | 6/1973 | Basiulis et al. | 128/303.1 |
| 3,776,241 A | 12/1973 | Magilton et al. | 128/400 |
| 3,897,790 A | 8/1975 | Magilton et al. | 128/400 |
| 4,010,795 A | 3/1977 | Stenberg | |
| 4,207,897 A | 6/1980 | Lloyd et al. | 128/303.1 |
| 4,719,919 A | 1/1988 | Marchosky et al. | 128/401 |
| 4,781,193 A | 11/1988 | Pagden | 128/402 |
| 4,860,744 A | 8/1989 | Johnson et al. | 128/303.1 |

(List continued on next page.)

FOREIGN PATENT DOCUMENTS

| | | |
|---|---|---|
| DE | 19521166 | 12/1996 |
| EP | B10132276 | 1/1985 |

(List continued on next page.)

OTHER PUBLICATIONS

Perov, et al., "Design of Thermodes for Cooling Sites of Cerebral Hemisphere Cortex in Chronic Tests", Sechenov Physiology Journal of the USSR, No. 7, 1983, methods of Physiological Investigations, 5 pgs.

Mursky, "On the Use of Complex (Cranial Cerebral and General) Hypotherma in Experiments", Brain Hypothermia, 1965, 4 pgs.

Shilo, et al., "Delivery/Dialysis Cannula for Local Superfusion of Brain Structures at Cranial Cerebral Hypothermia", Collection of Scientific Works, 1988, 3 pgs.

Rybakov, "Method of Intra–Ventricle Hypothermia of Brain", 3 pgs.

*Primary Examiner*—Brian L. Casler
*Assistant Examiner*—Lina R Kontos
(74) *Attorney, Agent, or Firm*—Christopher & Weisberg, P.A.

(57) ABSTRACT

A method and expandable device for thermally affecting tissue in which there is a fluid conduit. An expandable element includes a wall defining an inner volume. The wall has a tissue contact region which is non-coaxial with the longitudinal axis of the fluid conduit. The tissue contact region is operable to have a first contact surface area and a second contact surface area in which the second contact surface area is larger than the first contact surface area. A port is formed through the wall and is in fluid communication with the fluid conduit.

12 Claims, 4 Drawing Sheets

U.S. PATENT DOCUMENTS

| | | | |
|---|---|---|---|
| 4,946,460 A | 8/1990 | Merry et al. | 606/24 |
| 4,989,601 A | 2/1991 | Marchosky et al. | 128/399 |
| 5,108,407 A | 4/1992 | Geremia et al. | |
| 5,207,674 A | 5/1993 | Hamilton | 606/20 |
| 5,261,399 A | 11/1993 | Klatz et al. | 607/104 |
| 5,334,181 A | 8/1994 | Rubinsky et al. | 606/22 |
| 5,380,319 A | 1/1995 | Saito et al. | 606/28 |
| 5,417,686 A | 5/1995 | Peterson et al. | 606/25 |
| 5,429,582 A * | 7/1995 | Williams | 600/2 |
| 5,474,533 A | 12/1995 | Ward et al. | 604/26 |
| 5,520,682 A | 5/1996 | Baust et al. | 606/24 |
| 5,531,776 A | 7/1996 | Ward et al. | 607/105 |
| 5,540,711 A | 7/1996 | Kieturakis et al. | 606/192 |
| 5,549,559 A | 8/1996 | Eshel | 604/113 |
| 5,591,162 A | 1/1997 | Fletcher et al. | 606/25 |
| 5,607,443 A | 3/1997 | Kieturakis et al. | 606/192 |
| 5,609,620 A | 3/1997 | Daily | |
| 5,611,767 A | 3/1997 | Williams | 600/2 |
| 5,624,392 A | 4/1997 | Saab | 604/43 |
| 5,643,207 A | 7/1997 | Rise | 604/93 |
| 5,645,528 A | 7/1997 | Thome | 604/96 |
| 5,713,923 A | 2/1998 | Ward et al. | 607/3 |
| 5,716,353 A | 2/1998 | Matsuura et al. | 606/22 |
| 5,716,386 A | 2/1998 | Ward et al. | 607/106 |
| 5,718,584 A | 2/1998 | Wong | 433/168.1 |
| 5,718,684 A | 2/1998 | Gupta | 604/96 |
| 5,730,756 A | 3/1998 | Kieturakis et al. | 606/190 |
| 5,735,817 A * | 4/1998 | Shantha | 604/100.02 |
| 5,772,680 A | 6/1998 | Kieturakis et al. | 606/190 |
| 5,814,014 A | 9/1998 | Elsberry et al. | 604/43 |
| 5,817,123 A | 10/1998 | Kieturakis et al. | 606/192 |
| 5,843,075 A | 12/1998 | Taylor | 606/34 |
| 5,871,498 A | 2/1999 | Jervis et al. | 606/192 |
| 5,891,134 A | 4/1999 | Goble et al. | |
| 5,899,898 A | 5/1999 | Arless et al. | 606/22 |
| 5,913,885 A | 6/1999 | Klatz et al. | 607/104 |
| 5,916,212 A | 6/1999 | Baust et al. | 606/22 |
| 5,916,242 A | 6/1999 | Schwartz | 607/113 |
| 5,928,203 A | 7/1999 | Davey et al. | 604/247 |
| 5,951,512 A | 9/1999 | Dalton | 604/93 |
| 5,954,714 A * | 9/1999 | Saadat et al. | 606/28 |
| 5,957,963 A | 9/1999 | Dobak, III | 607/104 |
| 5,976,109 A | 11/1999 | Heruth | 604/140 |
| 6,004,337 A | 12/1999 | Kieturakis et al. | 606/190 |
| 6,015,382 A | 1/2000 | Zwart et al. | 600/207 |
| 6,015,421 A | 1/2000 | Echeverry et al. | 606/190 |
| 6,017,324 A | 1/2000 | Tu et al. | 604/96 |
| 6,030,412 A | 2/2000 | Klatz et al. | 607/104 |
| 6,042,579 A | 3/2000 | Elsberry et al. | 604/891.1 |
| 6,045,532 A | 4/2000 | Eggers et al. | 604/114 |
| 6,051,019 A | 4/2000 | Dobak, III | 607/104 |
| 6,053,913 A | 4/2000 | Tu et al. | 606/41 |
| 6,073,051 A | 6/2000 | Sharkey et al. | 607/99 |
| 6,074,412 A | 6/2000 | Mikus et al. | 607/105 |
| 6,083,148 A | 7/2000 | Williams | 600/2 |
| 6,090,132 A | 7/2000 | Fox | 607/96 |
| 6,096,068 A | 8/2000 | Dobak, III et al. | 607/105 |
| 6,106,518 A | 8/2000 | Wittenberger et al. | 606/23 |
| 6,113,593 A | 9/2000 | Tu et al. | 606/34 |
| 6,117,128 A | 9/2000 | Gregory | 606/7 |
| 6,122,549 A | 9/2000 | Sharkey et al. | 607/99 |
| 6,123,718 A | 9/2000 | Tu et al. | 607/113 |
| 6,126,680 A | 10/2000 | Wass | 607/96 |
| 6,126,684 A | 10/2000 | Gobin et al. | 607/113 |
| 6,129,736 A | 10/2000 | Jervis et al. | 606/192 |
| 6,132,415 A | 10/2000 | Finch et al. | 604/502 |
| 6,146,411 A | 11/2000 | Noda et al. | 607/105 |
| 6,149,677 A | 11/2000 | Dobak, III | 607/106 |
| 6,152,920 A | 11/2000 | Thompson et al. | 606/41 |
| 6,156,057 A | 12/2000 | Fox | 607/96 |
| 6,168,608 B1 | 1/2001 | Echeverry et al. | 606/190 |
| 6,179,831 B1 | 1/2001 | Bliweis | 606/21 |
| 6,183,501 B1 | 2/2001 | Latham | 607/109 |
| 6,248,126 B1 | 6/2001 | Lesser et al. | 607/113 |
| 6,304,214 B1 | 10/2001 | Aiken et al. | 607/105 |
| 6,322,559 B1 | 11/2001 | Daulton et al. | |
| 6,383,210 B1 | 5/2002 | Magers et al. | |

FOREIGN PATENT DOCUMENTS

| | | |
|---|---|---|
| EP | B10382787 | 8/1990 |
| EP | B10586567 | 3/1994 |
| JP | 5500858 | 12/1992 |
| JP | 5505399 | 3/1993 |
| JP | 1151900 | 9/2000 |
| JP | 11170076 | 11/2000 |
| JP | 2000126973 | 12/2000 |
| JP | 11290530 | 4/2001 |
| RU | 639557 | 6/1978 |
| RU | 432907 | 3/1979 |
| RU | 1544422 | 1/1996 |
| RU | 1745238 | 4/1997 |
| RU | 833266 | 9/1998 |
| RU | 1787026 | 9/1998 |
| RU | 211736 | 2/1999 |
| RU | 1138152 | 2/1999 |
| RU | 2100989 | 3/1999 |
| RU | 293381 | 3/2000 |
| WO | WO9603943 | 2/1996 |
| WO | WO9934758 | 7/1999 |
| WO | WO0007507 | 2/2000 |
| WO | WO0059419 | 10/2000 |
| WO | WO0117471 | 3/2001 |
| WO | WO0176517 | 10/2001 |

* cited by examiner

EXPANDABLE DEVICE FOR THERMAL THERAPY

CROSS-REFERENCE TO RELATED APPLICATION

This application is related to and claims priority to U.S. Provisional Patent Application Serial No. 60/238,314, filed Oct. 5, 2000, entitled SYSTEMS AND METHODS FOR CONTROLLING TEMPERATURE OF BRAIN TISSUE, the entirety of which is incorporated herein by reference.

STATEMENT REGARDING FEDERALLY SPONSORED RESEARCH OR DEVELOPMENT n/a

FIELD OF THE INVENTION

The present invention relates to a device and method for controlling brain tissue temperature, and in particular, to a device and method for sub-cranial temperature control of brain tissue through the use of expandable elements, such as balloons.

BACKGROUND OF THE INVENTION

The benefits of the application or removal of thermal energy to or from a localized portion of a tissue area to apply or remove thermal energy is well known in the art. Balloons are commonly used to contact a tissue. It is desirable to have a delivery device that facilitates the introduction of thermal energy to a tissue region. While it is known to use balloons to contact tissue surfaces along the length of a catheter that is inserted into a vessel, a need arises for a device to apply localized thermal energy in alternate treatment scenarios. For example, as is known in the art, it is desirable to be able to apply or remove thermal energy to or from the extreme end of a catheter.

It is also desirable to avoid creating unnatural openings in a human body. However, when a medical need mandates creating an opening, making as small an opening as possible is advantageous. The need to keep openings to a minimum is particularly applicable when dealing with openings in a human skull. However, a device is needed to apply or remove thermal energy to or from a tissue area with a larger surface area than the opening through which the catheter is inserted.

Problems of uniform thermal distribution also arise with known devices. When a thermally transmissive fluid is infused into a space, the distribution of thermal energy is governed by the function of thermal convection. As such, in many situations thermal energy is not evenly distributed throughout the space. Therefore, it is desirable to provide a device which evenly distributes or removes thermal energy from tissue.

SUMMARY OF THE INVENTION

According to an aspect of the present invention, an expandable device for thermally affecting tissue is provided in which a fluid conduit having a longitudinal axis is in fluid communication with an expandable element. The expandable element has a wall defining an inner volume. The wall has a tissue contact which is non-coaxial with the longitudinal axis of the fluid conduit. The tissue contact region is operable to have a first contact surface area and a second contact surface area. The second contact surface area is larger than the first contact surface area.

According to another aspect of the present invention, another expandable element for thermally affecting tissue is provided in which a port has a longitudinal axis and is in fluid communication with an expandable element. A wall defines an inner volume and the wall has a tissue contact region. The tissue contact region is non-coaxial with the longitudinal axis of the port. The tissue contact region is operable to have a first contact surface area and a second contact surface area. The second contact surface area is larger than the first contact surface area.

According to yet another aspect of the present invention, a method of using an expandable element to affect a thermal energy change in tissue of a patent's body is provided in which an opening is created in the patient's body. The expandable element is in fluid communication with a fluid conduit and has a tissue contact region that is non-coaxial with a longitudinal axis of the fluid conduit. The tissue contact region is operable to have a first contact surface area and a second contact surface area which is larger than the first contact surface area. At least a portion of the expandable element is inserted into the opening, having a first contact surface area, and into a region between an outer barrier of the patent's body and the tissue. The tissue contact region is then operated to the second contact surface area and infused with a thermally transmissive fluid, thereby affecting a thermal change in the tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention provides a device having an expandable surface area for the application or removal of thermal energy to/from a selected site. The present invention also provides a device that can be inserted through an opening in a patient's body and expanded or deployed to cover a greater surface area than a device whose contact surface area is less than or equal to the size of the opening or which occupies the surface area along a small portion of the length of the device. Further provided is a feature which deploys the expandable portion of the device and supplies the expandable portion with material which imparts or removes thermal energy from the selected tissue site.

Figure 1:
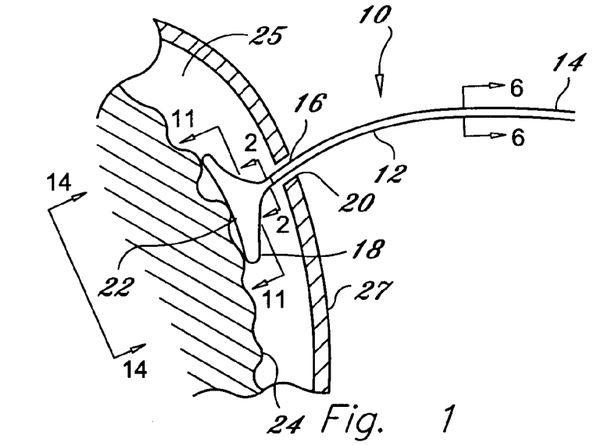
FIG. 1 is a perspective view of an exemplary embodiment of a device constructed in accordance with the principles of the present invention.

Referring now to the drawing figures in which like reference designators refer to like elements, there is shown FIG. 1 a perspective view of an exemplary embodiment of a device constructed in accordance with the principles of the present invention and designated generally as device 10. The device 10 includes a body 12 having a proximal end 14, a distal end 16 opposite the proximal end 14 and an expandable element 18 such as a balloon coupled to the distal end 16 of the body 12. The expandable element 18 is provided with a physical structure that allows the expandable element 18 to be inserted through a small opening 20 and then deployed, thereby expanding a tissue contact surface area 22. When deployed, the tissue contact surface area 22 has a surface area greater than when the expandable element 18 is not deployed, with which to contact a tissue 24. Further, expandable element 18 is arranged to be deployable within a region 25 between an outer barrier 27 and the tissue 24 without causing damage to tissue 24. An example of region 25 is found between the skull and the dura mater in a human. The tissue contact surface area 22 can have a shape ranging from substantially flat to concave or being flexible enough to conform to natural contours on the tissue surface.

In an alternate insertion procedure, the expandable element can be placed against the dura mater which has been exposed by a craniotomy. An opening is then made in the boney plate, removed during the craniotomy, for the body 12 of the device to pass through. When the boney plate is reattached to the skull, the expandable element remains within the epidural space, while the body 12 passes to the exterior of the skull. When removal of the expandable element is desired, the expandable element can then be "deflated" and removed through the opening in the boney plate. Additionally, many different ways to reach the boney material of a skull are contemplated. For example, the skin that lies directly adjacent the location of the desired opening in the boney material can be cut or removed to allow the device to transverse the skin layer. Alternatively, an incision can be made a distance from the opening in the boney plate and the device "tunneled" under the skin to the skull insertion point.

In an exemplary embodiment of the invention, the expandable portion of the device is provided by a bundled expandable element 18. The bundled expandable element 18 defines a diameter small enough to fit into a standard sized burr hole in a skull, such as 5 mm, 8 mm, 11 mm and 14 mm diameters. The expandable element 18 is then infused with chilled or heated fluid to expand its shape to a deployed state, the expansion causing contact with the tissue to be treated. The fluid can thereby impart a thermal change to the expandable element which in turn imparts a thermal change to the contacted tissue. Furthermore, the temperature of the fluid can be regulated such that a constant temperature can be maintained or specific cooling/heating regimens provided. The term fluid as used herein refers to a substance in a liquid state, a gaseous state, a transition state or a combination thereof.

It is further contemplated that a device in accordance with the principles of the present invention can be used to create an epidural pocket between the dura mater and the inner skull. For example, once the device is inserted into the opening and deployed, it will separate the dura from the inner skull, thereby creating an area for the device 10 to reside during a treatment. Alternatively, a discrete device or an attachment to the device 10 can be used to create the epidural pocket before deployment of the device 10. Further, it is contemplated that a hemostasis-inducing coating can be applied to the expandable element 18 to reduce bleeding that can occur during operation of the device 10. Alternatively, the device 10 can be equipped with a method for cauterizing the dura as the epidural pocket is created, thereby reducing bleeding that may occur.

FIG. 1 shows the expandable element 18 in association with a flexible body 12, however, it will be readily understood by one of ordinary skill in the art that any number of alternate structures may be used, for example any shaped expandable balloon element or multi-balloon elements having various sizes, shapes and diameters. Examples of expandable element 18 constructed in accordance with the principles of the present invention are described in greater detail below.

Figure 2:
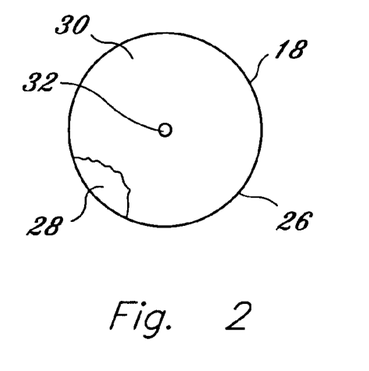
FIG. 2 is a top view of an expandable element of the invention.

FIG. 2 is a top view of the expandable element 18. As shown in FIGS. 1 and 2, the expandable element 18 is in a deployed state. Further, FIG. 2 shows the expandable element having a substantially circular planar view, however, it will be readily understood that other shapes may be provided as well, for example, an oval shape, an amorphous shape, a spiral shape or a spider-like shape as discussed below.

Figures 3, 4:
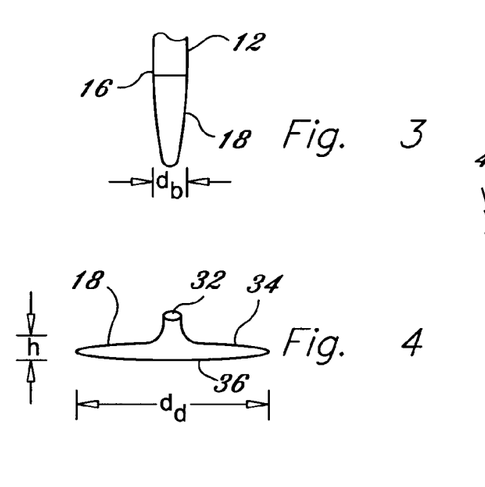
FIG. 3 illustrates a side view of the device shown in FIG. 1, in a bundled state.
FIG. 4 is a side view of the device shown in FIG. 1, in a deployed state.

The expandable element 18 has a wall 26 which defines an interior volume 28, shown in FIG. 2 in phantom cutaway. The wall 26 is constructed of a resilient material that provides the ability to "deflate" or bundle the expandable element 18 into a bundled state, as shown in FIG. 3. Exemplary resilient materials include rubber, silicon, flexible and thermoplastic polymers.

Turning back to FIG. 2, the expandable element has a proximal side 30 which is opposite the tissue contact surface area 22 (not shown here) which may contact the skull. Provided on the proximal side 30 is a port 32. The port 32 has a longitudinal axis extending through a center of the port 32. FIG. 2 shows the port 32 positioned substantially in the center of the expandable element 18 on the proximal side 30. However, it will be readily understood by those skilled in the art that port 32 can be positioned in alternate locations, for example along the periphery of wall 26.

FIG. 3 illustrates a side view of the expandable element 18 shown in FIG. 1 in a bundled state. FIG. 3 shows the expandable element 18 having a bundled diameter $d_b$ which preferably ranges in size up to 14 mm.

FIG. 4 is a side view of the expandable element 18 shown in FIG. 1 shown in the deployed state. In FIG. 4, the port 32 is provided substantially in the center of expandable element 18. However, it will be readily understood that port 32 can be provided at alternate locations on the expandable element 18. The port 32 provides a fluid communication pathway between the expandable element 18 and the body 12 (not shown). The port 32 is also in fluid communication with the interior volume 28 (not shown). As such, when the body 12 (not shown) is in fluid communication with the port 32, the body 12 is also in fluid communication with the interior volume 28. Alternate configurations of a connection arrangement between the body 12, the port 32 and the interior volume 28 are discussed in further detail below. Expandable element 18 has a deployed diameter "$d_d$" measured at the widest part along the wall and a height "h" measured from a top 34 of the expandable element 18 to a bottom 36 of the expandable element 18. A circular expandable element 18 constructed in accordance with the principles of the present invention can have a deployed diameter $d_d$ ranging in size from 5 to 200 mm. An exemplary embodiment has a deployed diameter $d_d$ of 48 mm. Another exemplary embodiment has a deployed diameter $d_d$ of 64 mm. Further, an exemplary embodiment can have a height h ranging in size from 1 to 10 mm. In one exemplary embodiment the height h is approximately 5 mm.

Figure 5:
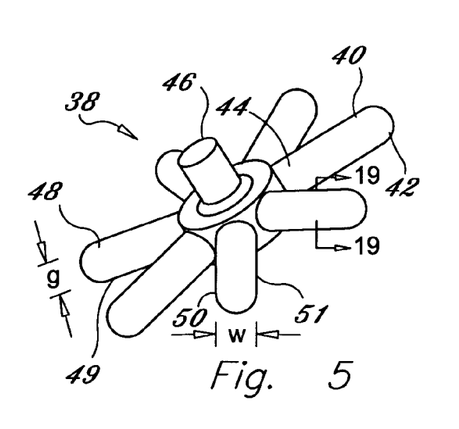
FIG. 5 shows a perspective view of an alternate embodiment of an expandable portion of the device constructed in accordance with the principles of the present invention.

FIG. 5 shows a perspective view of an alternate embodiment of the expandable element 18, shown as a shaped expandable element 38. The shaped expandable element 38 has at least one expandable element arm 40 which has a distal end 42 and a proximal end 44 opposite the distal end 42, in which each expandable element arm 40 is joined at the proximal end 44 to a port 46 to create a "spider-like" expandable element arrangement. Each expandable element arm 40 has a height "g" measured from a top 48 of the expandable element arm 40 to a bottom 49 of the expandable element arm 40. Further, each expandable element arm 40 has a width "w" measured from a first side 50 of the expandable element arm 40 to a second side 51 of the expandable element arm 40. Further, each expandable element arm 40 preferable has approximately a 2 to 1 width w to height g ratio. The materials used to construct the shaped expandable element 38 include one or more of compliant, non-compliant, and partially compliant polymers.

In use, deployment of the shaped expandable element 38 occurs as with the above-described expandable element 18. Alternately, deployment of a plurality of the expandable element arms 40 can occur individually. The ability to selectively deploy individual expandable element arms 40 is provided by an individual injection member for each expandable element arm 40 (injection members are more fully discussed below). In practice, an injection member that corresponds to an individual expandable element arm 40 is provided with a flow of thermal fluid, which thereby inflates or deploys the corresponding expandable element arm 40. The above described shaped expandable element can be manufactured by standard polymer tube technology processes.

Figures 6, 7:
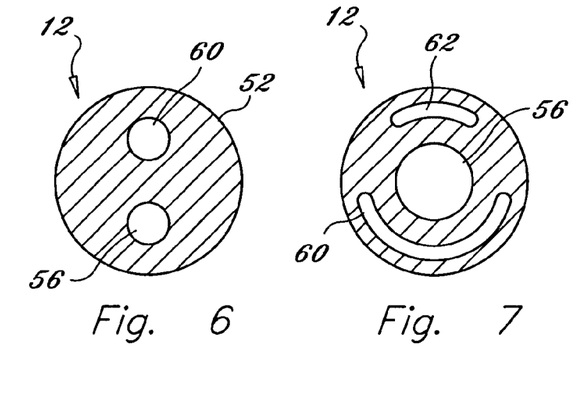
FIG. 6 is a sectional view of the device taken along section 6—6 in FIG. 1.
FIG. 7 is an alternate sectional view of the device taken along section 6—6 in FIG. 1.

FIG. 6 is a sectional view of the body 12 taken along section 6—6 in FIG. 1. The body 12 has a body wall 52 which defines at least one lumen. An inlet conduit 56 provides a conduit for the infusion of a fluid into the expandable element 18. Further, an outlet conduit 60 provides a conduit for removal of a fluid from the expandable element 18. However, it is contemplated that the functions of the inlet conduit 56 and the outlet conduit 60 can be reversed.

When the body 12 is connected to the expandable element 18, the inlet conduit 56 and the outlet conduit 60 are in fluid communication with the interior volume 28. As such, fluids can be introduced and evacuated from the interior volume 28 by way of the inlet conduit 56 and the outlet conduit 60 of the body 12. Further, the body 12 can be a catheter which allows a user to position the expandable device 10 at a tissue treatment site.

FIG. 7 is an alternate sectional view of the body 12 taken along section 6—6 in FIG. 1. FIG. 7 shows the inlet conduit 56 provided substantially coaxial with the longitudinal axis of the body 12. Further, the outlet conduit 60 is provided with a elongated shape along a partial portion of the outer circumference of the inlet conduit 56. Additionally, a conduit 62 located along the outer circumference of the inlet conduit 56 and opposite the outlet conduit 60 is provided for carrying accessory components, such as temperature and/or pressure sensor lead lines (not shown). It will be readily understood by one skilled in the art that either the first or second lumen can interchangeably act as an inlet conduit or an outlet conduit.

Figure 8:
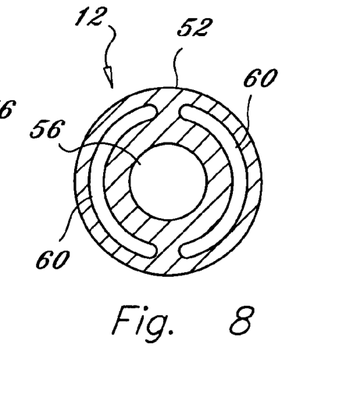
FIG. 8 is another alternate sectional view of the device taken along section 6—6 in FIG. 1.

FIG. 8 is another alternate sectional view of the body 12 taken along section 6—6 in FIG. 1. FIG. 8 shows the inlet conduit 56 centered within the body wall 52 of the body 12 and two outlet conduits 60 provided around a portion of the outer circumference of the inlet conduit 56 within the body 12.

Figure 9:
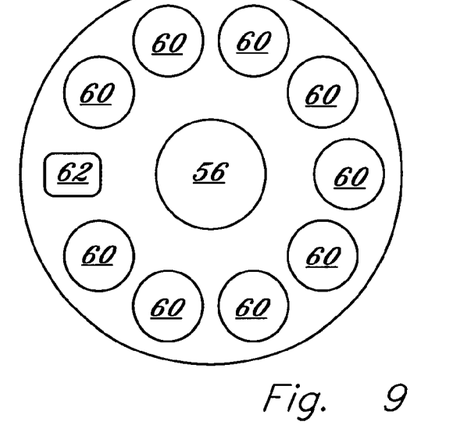
FIG. 9 is still another alternate sectional view of the device taken along section 6—6 in FIG. 1.

FIG. 9 is another alternate sectional view of the body 12 taken along section 6—6 in FIG. 1. FIG. 9 shows a plurality of outlet conduits 60 and a centrally located inlet conduit 56 provided around a portion of the outer circumference of the outlet conduit 60 within the body 12. Optionally, a conduit 62 can be provided to carry accessory components as discussed herein.

From these examples, it will readily understood that many alternate arrangements can be made. For example, one or more accessory conduits can be provided in any of the above disclosed configurations, the first and second lumens can act as either inlet or outlet conduits and additional structures may be incorporated.

Figure 10:
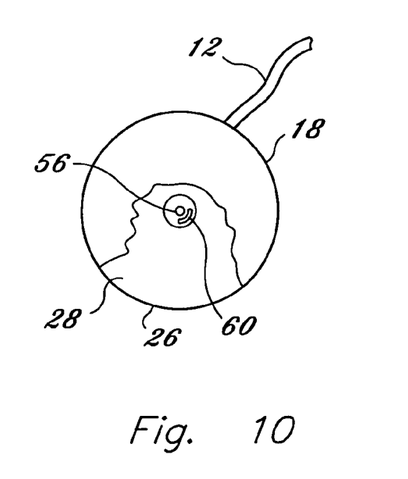
FIG. 10 shows a cut-away perspective view of the device in a deployed state.

FIG. 10 shows a cut-away perspective view of the expandable portion of the device in a deployed state. Referring to FIG. 10, operation of this exemplary embodiment is discussed. In use, the thermally transmissive fluid is transferred into the interior volume 28 through the inlet conduit 56 and evacuated from the interior volume 28 through the outlet conduit 60. Circulation of the thermally transmissive fluid within the interior volume 28 transmits or removes thermal energy to or from the expandable element wall 26 by convection, which characteristics are known to those skilled in the art. It is contemplated that a steady thermal state can be maintained between the treatment site and the expandable element 18 or that desirable thermal changes can be affected.

Additionally, the present invention distributes the thermally transmissive fluid in order to thermally control portions along the surface of the device 10. It is contemplated that many different methods of distributing the fluid can be used. Several exemplary fluid distribution methods are described herein. One such method is provided by supplying a fluid distribution feature within the expandable element 18, embodiments of which are discussed in more detail below.

Figure 11:
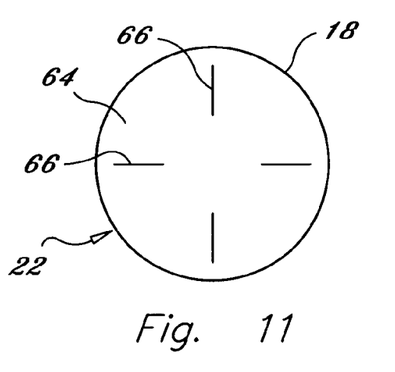
FIG. 11 is a planar view of a fluid distribution element of a device constructed in accordance with the principles of the present invention.

FIG. 11 is a sectional planar view taken along section 11—11 in FIG. 1. FIG. 11 shows an interior surface 64 of the contact surface 22, which is disposed within the interior volume 28 of the expandable element 18. Affixed to the interior surface 64 is at least one vane 66. It is contemplated that one or more vanes 66 can be used and that their shape can be varied to advantageously affect fluid distribution within the interior volume 28 or to affect structural shape of the bundled or deployed expandable element. For example, FIG. 11 shows four vanes 66 extending radially from a center longitudinal axis to an outside periphery of the expandable element 18. The vanes 66 define flow pathways for the thermally-transmissive fluid. The vanes 66 can be small ridges of protruding material or other such raised structures. As such, the vanes provide for even distribution of the thermally transmissive fluid within the interior volume 28, thereby reducing areas of uneven temperature. It will be readily understood by one of ordinary skill in the art that different configurations can be employed to efficiently distribute thermally-transmissive fluid within the interior volume 28 of the expandable element 18 or to selectively distribute the thermally-transmissive fluid to specific portions of the interior volume 28.

Figure 12:
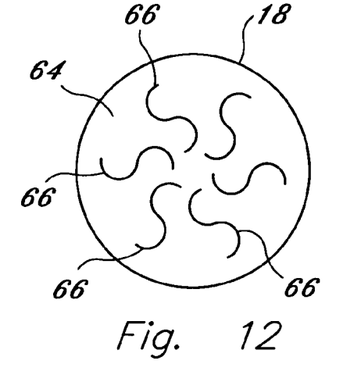
FIG. 12 is an alternate planar view of a fluid distribution element of a device constructed in accordance with the principles of the present invention.

FIG. 12 shows another embodiment of a fluid distribution element with a greater number of vanes 66. FIG. 12 shows a plurality of "S"-shaped vanes 66 affixed to the interior surface 64 and extending radially outward from a center longitudinal axis. It is contemplated that the vanes 66 are affixed to other surfaces in communication with the interior volume 28. Further, the vanes 66 can be free-floating within the interior volume 28.

Figure 13:
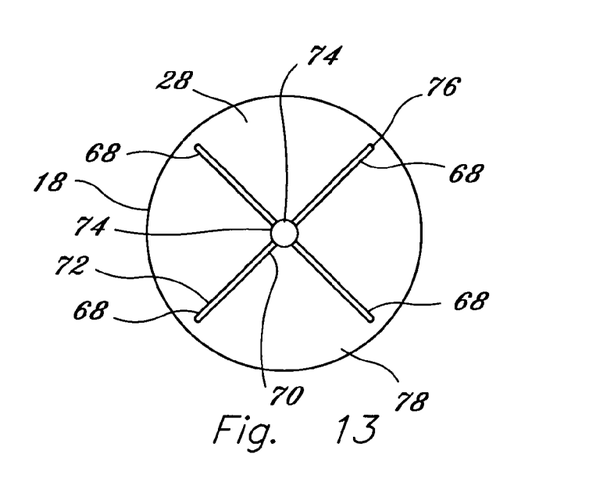
FIG. 13 shows a cut-away end view of a device in a deployed state constructed in accordance with the principles of the present invention.

FIG. 13, shows a cut-away end view of an expandable device in a deployed state constructed in accordance with the principles of the present invention. FIG. 13 shows the interior volume 28 having at least one injection member 68 provided therein. FIG. 13 shows four such injection members 68. However, it will be readily understood that various configurations may be provided.

Focusing on one injection member 68, the injection member 68 has a proximal end 70 and a distal end 72. The proximal end 70 is in fluid communication with the inlet conduit 56 of the body 12 (not shown and as described above). A junction 74 is provided to facilitate connection of the injection member 68 to the inlet conduit 56, however, other arrangements without a junction 74 can also be employed, as discussed herein. Further, the distal end 72 defines an opening 76 for fluid output flow. Alternatively, an injection member 68 could have one or more openings 76 along a length of the injection member 68, whether an opening at the distal end 72 is provided or not. Although all of the exemplary injection members 68 are shown in FIG. 13 as having equal lengths, it is contemplated that each individual injection member 68 can have the same or a length different from at least one other injection member 68. Additionally, the injection member 68 can be extruded from a urethane/pellethane material having a relatively soft durometer or manufactured by other processes know in the art.

Referring to FIGS. 1 and 13 operation of the device is discussed, in use, thermally transmissive fluid is infused into the inlet conduit 56 at the proximal end 14 of the body 12. The fluid then passes to the distal end 16 of the body 12 and through the injection member 68, which directs the fluid to pre-specified locations within the interior volume 28. In an exemplary embodiment the fluid is directed to a periphery 78 of the expandable element 18. The thermally transmissive fluid thereby imparts or removes thermal energy from the tissue contact surface area 22. The tissue contact surface area 22 can then affect a temperature of the tissue at a treatment site. The fluid is then evacuated from the interior volume 28 via the outlet conduit 60 and returned to the proximal end 14 of the body 12 for recovery or reuse. This process can be a continuous flow or can be regulated in cycles or steps.

As such, the thermally transmissive fluid is directed to a pre-selected area of the interior volume 28 to provide for a reduction in the occurrence of uneven temperature areas within the interior volume 28. Further, it is contemplated that different lengths and different numbers of injection members 68 can be used to optimize a desired temperature distribution. Further still, different temperature zones at different locations over the tissue contact surface area 22 of the expandable element 18 can be provided as desired.

Figures 14, 16:
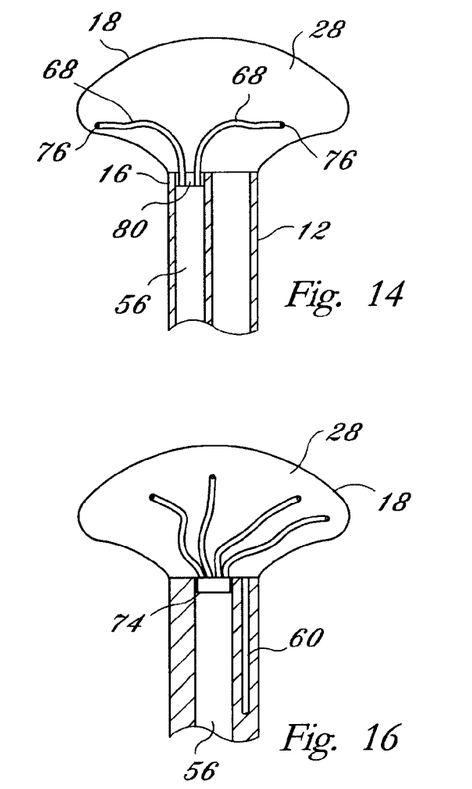
FIG. 14 is a sectional view of an exemplary interface region of the device taken along section 14—14 in FIG. 1.
FIG. 16 is a cross-sectional view of an exemplary interface region of the device taken along section 14—14 in FIG. 1.

FIG. 14 is a sectional view of an exemplary interface region taken along section 14—14 in FIG. 1. For exemplary purposes only, FIG. 14 shows a body 12 configuration as shown in FIG. 6, however, it is contemplated that other body 12 configurations can be provided. A filler 80 forms a fluid tight seal between the inlet conduit 56 and the injection members 68, thereby providing a path of fluid communication from the inlet conduit 56 to the openings 76 and in turn, to the interior volume 28 of the expandable element 18. Further, the filler 80 is any suitable material having bonding properties, for example, silicone, rubber, flexible polymers, epoxies or other bonding components. FIG. 14 shows two injection members 68, however, it is contemplated that any quantity of injection members 68 can be provided.

Figure 15:
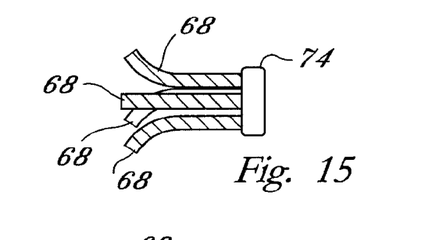
FIG. 15 is a perspective view of a junction of a device constructed in accordance with the principles of the present invention.

FIG. 15 is a perspective view of a junction 74 of a device constructed in accordance with the principles of the present invention. A junction 74 can be formed from the filler 80 described above, formed from a "plug" of material or other methods may be employed, for example, the junction 74 can be machined or injection molded.

A plurality of injection members 68 are attached and in fluid communication with the junction 74. In turn, junction 74 is attached to and in fluid communication with the inlet conduit of the body 12, as discussed below. FIG. 14 shows four injection members 68, however, it is contemplated that any quantity of injection members 68 can be provided.

FIG. 16 is a sectional view of another exemplary interface region taken along section 14—14 in FIG. 1. Junction 74 is disposed at least partially within the inlet conduit 56 and is fixedly attached and in fluid communication therewith. The junction 74 is attached to the inlet conduit 56 by methods known in the art. Additionally, outlet conduit 60 is shown in partial sectional view. Both the injection members 68 and the outlet conduit 60 are in fluid communication with the interior volume 28 of the expandable element 18. For exemplary purposes only, FIG. 16 depicts a body 12 configuration as shown in FIG. 7, however, it is anticipated that alternate configurations can be provided.

Figure 17:
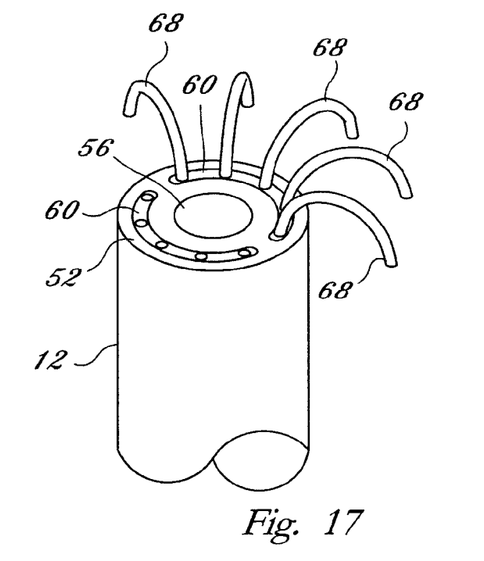
FIG. 17 is a cut-away, perspective view of an alternate arrangement of a junction of a device constructed in accordance with the principles of the present invention.

FIG. 17 is a cut-away, perspective view of an alternate body arrangement constructed in accordance with the principles of the present invention. FIG. 17 shows a plurality of injection members 68 disposed within outlet conduits 60 which are located inside a portion of the periphery of the body wall 52 (some shown in cut-away). Further the inlet conduit 56 is provided in the center of the body 12.

Figure 18:
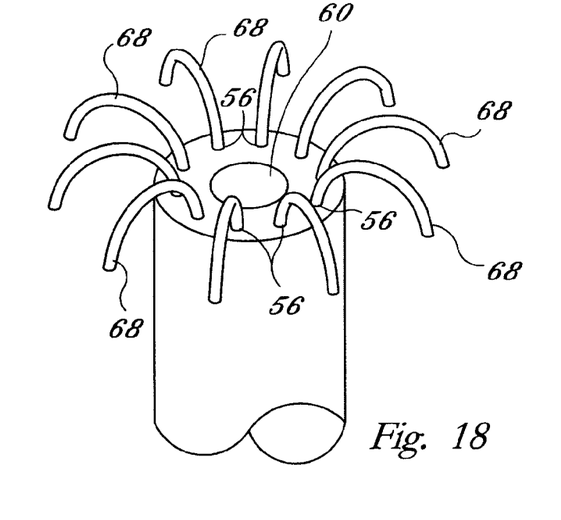
FIG. 18 is a cut-away, perspective view of still another alternate arrangement of a junction of a device constructed in accordance with the principles of the present invention.

FIG. 18 is a cut-away, perspective view of another alternate body arrangement constructed in accordance with the principles of the present invention. FIG. 18 shows a plurality of injection members 68 disposed within a plurality of inlet conduits 56. A centrally located outlet conduit 60 is also provided.

Figure 19:
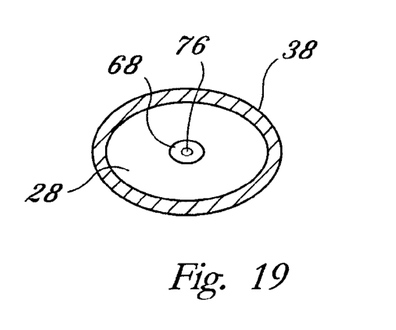
FIG. 19 is a sectional view taken along section 19—19 in FIG. 5.

FIG. 19 is a sectional view taken along section 19—19 in FIG. 5 constructed in accordance with the principles of the present invention. FIG. 19 shows a expandable element arm 38 having an arm wall which defines the interior volume 28. Provided within the interior volume 28 is an injection member 68 having an opening 76 which is in fluid communication with the interior volume 28. It is contemplated that all or some of the expandable element arms 40 shown in FIG. 5 can have an injection member 68 provided therein. The attendant advantages of such an arrangement are discussed with reference to other expandable element configurations herein. For example, temperature control along the expandable element arms 40 and selective deployment of individual arms can be provided.

Figure 20:
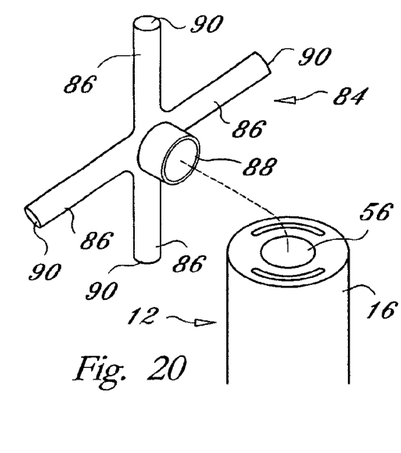
FIG. 20 is a perspective view of an alternate embodiment of a device constructed in accordance with the principles of the present invention.

FIG. 20 is a perspective view of an alternate embodiment of an injection member arrangement constructed in accordance with the principles of the present invention. FIG. 20 shows an alternate injection member arrangement having a unitary structure 84 which includes at least one injection tube arm 86. Further, unitary structure 84 has an inlet port 88. The injection tube arm 86 defines a tip opening 90. The unitary structure 84 is configured so that inlet port 88 is fixedly attached to inlet conduit 56 at the distal end 16 of the body 12. The entire unitary structure 84 is enveloped by the expandable element 18 (not shown). In practice, thermally conductive fluid is introduced into the unitary structure 84 and then flows into the expandable element 18 via tip opening 90. As such, the expandable element 18 is "inflated" with thermally conductive fluid, which thereby affects the temperature of the expandable element.

Figure 21:
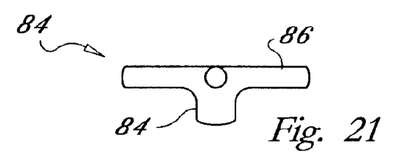
FIG. 21 is a side view of an alternate fluid distribution element of a device constructed in accordance with the principles of the present invention.
Figure 22:
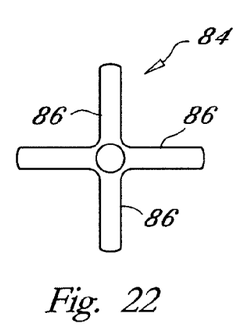
FIG. 22 is an overhead view of the fluid distribution element shown in FIG. 21.
Figure 23:
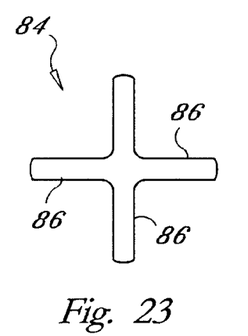
FIG. 23 is an bottom view of the fluid distribution element shown in FIG. 21.

FIGS. 21, 22 and 23 are side, overhead and bottom views respectively, each showing the unitary structure 84. While four injection tube arms 86 are shown, it is understood that other arrangements having fewer or greater quantities of injection tube arms 86 can be provided. The unitary structure 84 can be constructed from flexible material by casting, extruding or other suitable means. For example, injection molding can be used.

Figure 24:
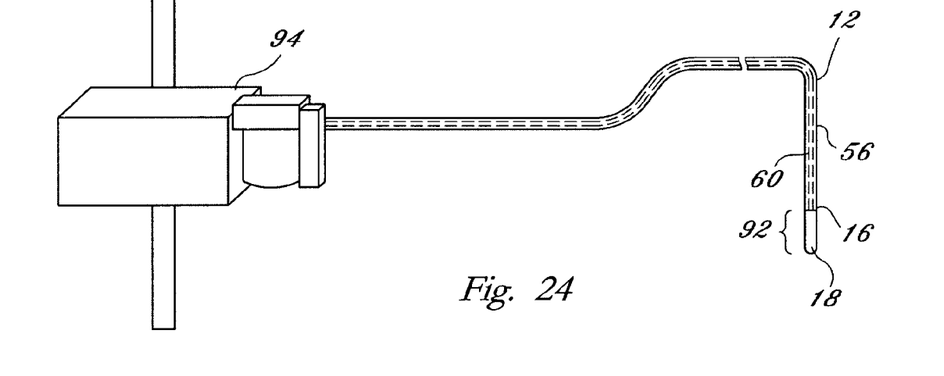
FIG. 24 is a perspective view of an exemplary system in a bundled state constructed in accordance with the principles of the present invention.

FIG. 24 is a perspective view of an exemplary system constructed in accordance with the principles of the present invention. An expandable element 18 is in a bundled state attached to the distal end 16 of the body 12. FIG. 24 shows inlet conduit 56 and outlet conduit 60 in phantom lines. Inlet conduit 56 is in fluid communication with a thermally-conductive fluid source 94 via body 12. Further, inlet conduit 56 is in fluid communication with the interior volume 28 (not shown) of the expandable element 18. Further still, the outlet conduit 60 is in fluid communication with the interior volume 28 (not shown) of the expandable element 18. The outlet conduit is in fluid communication with the thermally-conductive fluid source 94 via body 12. Inlet conduit 56 and outlet conduit 60 are in fluid communication with the interior volume 28 of the expandable element 18 and define a fluid circulation circuit.

In practice, the expandable element 18 is inserted in its bundled state 92 into the body of a subject to be treated. When the expandable element 18 is positioned at a desired treatment region, fluid is introduced into the expandable element 18 via the thermally-conductive fluid source 94—body 12 circuit, thereby "deploying" the expandable element. When the expandable element is in its deployed state, the fluid continues to flow through the circuit and thereby thermally affects the expandable element 18, which thereby thermally affects the tissue treatment site.

Figure 25:
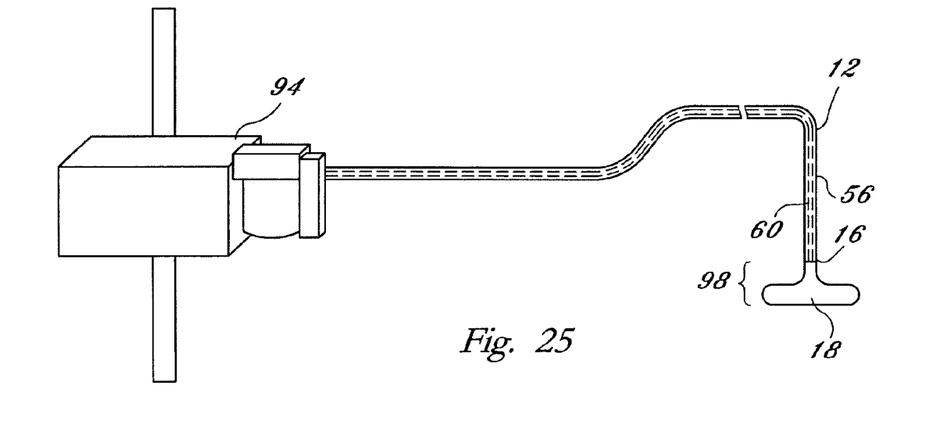
FIG. 25 is a perspective view of an exemplary system in a deployed state constructed in accordance with the principles of the present invention.

FIG. 25 is a perspective view of the exemplary system of FIG. 24 showing the expandable element 18 in a deployed state 98. For the sake of simplicity, those elements described with respect to FIG. 24 are not again described.

In practice, once the expandable element 18 is deployed, the thermally-transmissive fluid enters the interior volume 28 of the expandable element 18 through inlet conduit 56 thereby thermally affecting the wall 26 of the expandable element 18 by convection. At or about the same time, outlet conduit 60 excavates the thermal-transmissive fluid from the interior volume 28 of the expandable element 18. In this manner, the thermally-transmissive fluid affects a specific, controlled temperature to the wall 26 of the expandable element 18. Additionally, the wall 26 of the expandable element 18 can be fully or partially perfusive of fluid, to thereby allow fluid to directly contact tissue for treatment purposes. In addition, a medicament or other treatment fluid can be administered in this manner.

It is contemplated that the expandable element 18 can be deployed by various methods, for example, by inflation with the thermally-transmissive fluid, by mechanical supports, by employing a built-in biased shape of the expandable element 18, or other methods known in the art.

Specific construction of exemplary embodiments is now discussed in more detail. Expandable element and shaft materials are varied to accommodate specific applications. When used in an exemplary application, such as epidurally in the skull, to control temperature locally in the brain, the materials are preferably soft and pliable, for example composed of silicone polymer, soft pellethane (such as pellethane 80AE) or Pebax 42. Other applications may require the expandable element to have separate characteristics such as more durability or different compliant/non-compliant requirements. The thermally-transmissive fluid can be saline or a refrigerant which is cooled by a thermoelectric cooler or a refrigerant fluid. It is noted that cooled fluid can be used to chill cerebrospinal fluid.

Exemplary uses of the devices of the invention are now discussed in more detail. The above-described devices advantageously provide a physician with a way to control the temperature of a localized region of brain tissue by infusing a chilled or heated thermally-transmissive fluid, such as saline, into the expandable element and allowing convection to complete the thermal transfer between the localized brain tissue and the expandable element. This is preferably accomplished through a burr hole in the skull.

The exemplary application advantageously provides a chilled fluid in order to lower the localized brain temperature as a neuroprotective means in a cerebral ischemia condition. Also it is contemplated that the above-described device can additionally be used to cool localized regions of the brain in a brain trauma patient as a way to lower cerebral metabolic requirements and minimize brain edema. Furthermore, the device can also be used in any post-operative trauma situation when the possibility of cerebral edema exists and it is desired to be abated or minimized.

It is contemplated that the device described above can also be used in alternate procedures, for example, the device can be placed through the nose into the ethmoid sinus (neck skull bone) to cool carotid blood as it courses through the cavernous sinus up to the brain. Further, the device can be placed adjacent the hypothalamus and a warmed fluid circulated through the device to raise the temperature perceived by the hypothalamus, thereby triggering peripheral vasodilation and systemic cooling.

Further, the above described device can be used in other parts of the body in instances where local tissue temperature needs to be controlled or modulated. In such instances, thermal therapy may involve either chilled or heated fluid inside the expandable element to achieve the desired result. For example, the device could be applied to organs prior to or post transplant (e.g. kidney) to minimize ischemia and swelling. Further, the device could use be used to minimize uterine irritability in a female subject that is at risk for premature delivery.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An expandable element for thermally affecting tissue, comprising:
    a port, the port having a longitudinal axis; and
    a wall defining an inner volume, the wall having a tissue contact region, the tissue contact region being expandable when infused with the thermal fluid, the port being formed through the wall; and
    a fluid distribution member provided within the interior volume of the expandable member and affixed to the wall.

2. The device according to claim 1, wherein the expandable member is a balloon.

3. The device according to claim 1, wherein the expandable element has a non-circular shape.

4. The device according to claim 1, wherein the wall is configured to define a substantially circular shape.

5. The device according to claim 1, wherein the expandable element is comprised of a plurality of expandable arms.

6. The device according to claim 1, wherein the fluid distribution member is a vane.

7. The device according to claim 1, wherein the tissue contact region is aligned substantially parallel to the longitudinal axis of the port.

8. The device according to claim 5, further comprising at least one fluid injection member in fluid communication with the port, at least a portion of each of the at least one fluid injection members being enclosed within a corresponding expandable arm.

9. The device according to claim 8, wherein each expandable arm encloses at least a part of a corresponding fluid injection member.

10. The device according to claim 8, wherein each of the plurality of expandable arms are individually expandable.

11. An expandable device using thermal fluid from a fluid source for thermally affecting cranial tissue, comprising:
    a fluid conduit having a longitudinal axis;
    at least one injection element in fluid communication with the fluid conduit, the at least one injection element having a soft durometer;
    an expandable element in fluid communication with the fluid conduit, the expandable element including:
        a wall defining an inner volume and enclosing at least a portion of the at least one injection element, the wall having a tissue contact region, the tissue contact region being expandable when infused with the thermal fluid,
        the expandable element being insertable into an opening in a cranium when the expandable element is in an unexpanded state; and
        a fluid distribution member provided within the interior volume of the expandable member and affixed to the wall.

12. The device according to claim 11, wherein the fluid distribution member is a vane.

* * * * *